United States Patent [19]

Yashiro et al.

[11] Patent Number: 4,912,987
[45] Date of Patent: * Apr. 3, 1990

[54] MEASUREMENT OF SIZES OF FALLING PARTICLES

[75] Inventors: Hirokatsu Yashiro; Jiro Ohno, both of Kawasaki; Yoshiteru Matsuo, Kimitsu; Hiroshi Nishikawa, Kimitsu; Katsuhiko Yui, Kimitsu; Hirotoshi Kawamura, Kitakyushu, all of Japan

[73] Assignee: Nippon Steel Corporation, Tokyo, Japan

[*] Notice: The portion of the term of this patent subsequent to Jul. 4, 2006 has been disclaimed.

[21] Appl. No.: 317,973

[22] Filed: Mar. 2, 1989

Related U.S. Application Data

[60] Continuation of Ser. No. 95,967, Sep. 14, 1987, Pat. No. 4,843,894, which is a continuation-in-part of Ser. No. 851,148, Apr. 11, 1986, abandoned.

[30] Foreign Application Priority Data

Apr. 11, 1985 [JP] Japan .................................. 60-77343
Dec. 19, 1985 [JP] Japan ................................ 60-284445

[51] Int. Cl.$^4$ .......................................... G01N 15/02
[52] U.S. Cl. ................................ 73/865.5; 250/341; 356/336
[58] Field of Search ............. 73/1 R, 865.5; 356/335, 356/336; 250/341, 347, 349, 340, 342, 338 GA, 339

[56] References Cited

U.S. PATENT DOCUMENTS

| | | | |
|---|---|---|---|
| 3,317,730 | 5/1967 | Hilsum | 250/338 GA |
| 3,917,957 | 11/1975 | Ansevin et al. | 356/436 |
| 4,092,535 | 5/1978 | Ashkin et al. | 250/292.1 |
| 4,197,457 | 4/1980 | Cheo | 250/339 |
| 4,380,392 | 4/1983 | Karabegov et al. | 356/336 |
| 4,381,544 | 4/1983 | Stamm | 324/330 |
| 4,387,997 | 6/1983 | Adrian | 356/336 |
| 4,490,043 | 12/1984 | Cramp | 250/338 GA |
| 4,518,861 | 5/1985 | Krempl et al. | 250/343 |
| 4,525,627 | 6/1985 | Krempl et al. | 250/340 |
| 4,595,291 | 6/1986 | Tatsuno | 356/336 |
| 4,647,780 | 3/1987 | Dunkel | 356/438 |
| 4,652,755 | 3/1987 | Solomon et al. | 250/338 GA |
| 4,701,051 | 10/1987 | Buchhave et al. | 356/336 |

FOREIGN PATENT DOCUMENTS 6055252 3/1985 Japan .
0807141 2/1981 U.S.S.R. ............................ 356/336

OTHER PUBLICATIONS

Translation of Hirata. '252 cited above.
Definition of "electromagnetic spectrum"; American Heritage Dictionary.
Inaba et al.; "IR Lasar Radiation Technique Using Heterodyne Detection FOr Range-Resolved Sensing of Air Pollutants"; Optics Communication; vol. 14, No. 1; May 1975.

*Primary Examiner*—Robert R. Raevis
*Attorney, Agent, or Firm*—Wenderoth, Lind & Ponack

[57] ABSTRACT

For measuring the sizes of particles in the falling state, electromagnetic waves having different frequencies are transmitted from a transmitter/receiver onto the particles in the falling state and reflected electromagnetic waves having different frequencies reflected from the particles in the falling state are received by the transmitter/receiver. Data of the distribution of sizes of the particles and the average size of the particles are derived from the detected intensities of the received reflected electromagnetic waves.

8 Claims, 13 Drawing Sheets 4,912,987

MEASUREMENT OF SIZES OF FALLING PARTICLES

This application is a continuation of application Ser. No. 095,967, (now U.S. Pat. No. 4,843,894) filed on Sept. 14, 1987, which in turn was a continuation-in-part of application Ser. No. 851,148, filed on Apr. 11, 1986, claiming priority based on Japanese Patent Application Nos. 60-77343 and 60-284445, filed on Apr. 11, 1985 and Dec. 19, 1985, respectively.

BACKGROUND OF THE INVENTION

1. Field of the Invention

The present invention relates to a method and apparatus for measuring the sizes of particles in a falling state. The method and apparatus according to the present invention is used, for example, for measuring the size of iron ore or coke falling into a blast furnace in the iron industry.

2. Description of the Related Art

It is often necessary to continuously measure the sizes of particles which are in the falling state when being supplied into a vessel or the like.

In the operation of a blast furnace in the iron industry, materials such as iron ore and coke are accumulated in a charging hopper at the top of the blast furnace and are caused to fall intermittently into the blast furnace.

The thus falling materials have a great influence on the flow of gas in the blast furnace, which is a very important factor in maintaining a stable and efficient operation of the blast furnace, depending on the sizes of the particles of the materials. Also, segregation of the particle materials is often carried out while the particle materials are being transferred by a conveyor or the particle materials are going down through the charging hopper, depending on the sizes of particles of the particle materials. For these reasons, it is necessary to measure the sizes of particles of the particle materials immediately before the particle materials are charged into the blast furnace.

In the prior art, however, sizing of the particles has been carried out only by taking a certain amount of the particles as a sample from the particles which are being transferred by a conveyor and measuring the sizes of the sampled particles by a screen. A steady and continuous measurement technique for measuring the sizes of particles has not been established.

A method for measuring the sizes of minute particles such as those having a size of less than several hundred micro-meters in the falling state by using the diffraction of a laser light is disclosed in the Transactions of Japanese Mechanical Engineers Society, Vol 49, No. 442, Pages 2.30 to 2.38, June, 1983. However, this method cannot be applied to particle materials which are being charged into the blast furnace in a large amount, such as several hundred kilograms per second, wherein the particles have a size of several millimeters to several tens of millimeters and are falling within a cylinder having a diameter of several tens of centimeters, which does not permit the transmission of laser light.

SUMMARY OF THE INVENTION

It is an object of the present invention to provide a method and apparatus for measuring the sizes of particles in the falling state in an on-line and continuous manner, with as little limitation of the measurement conditions, such as the amount of falling particles, measurement environment, state of dispersion of the particles, or the like, as possible.

According to the fundamental aspect of the present invention, there is provided a method for measuring the sizes of particles in the falling state including the steps of: irradiating electromagnetic waves having diffferent frequencies onto particles in the falling state at a predetermined angle with respect to the direction in which the particles are falling and receiving reflected electromagnetic waves having different frequencies reflected from the particles in the falling state; detecting the intensities of the received reflected electromagnetic waves having different frequencies; and deriving data of the distribution of sizes of the particles and the average size of the particles from the detected intensities of the received reflected electromagnetic waves.

DESCRIPTION OF THE PREFERRED EMBODIMENTS

Figure 1:
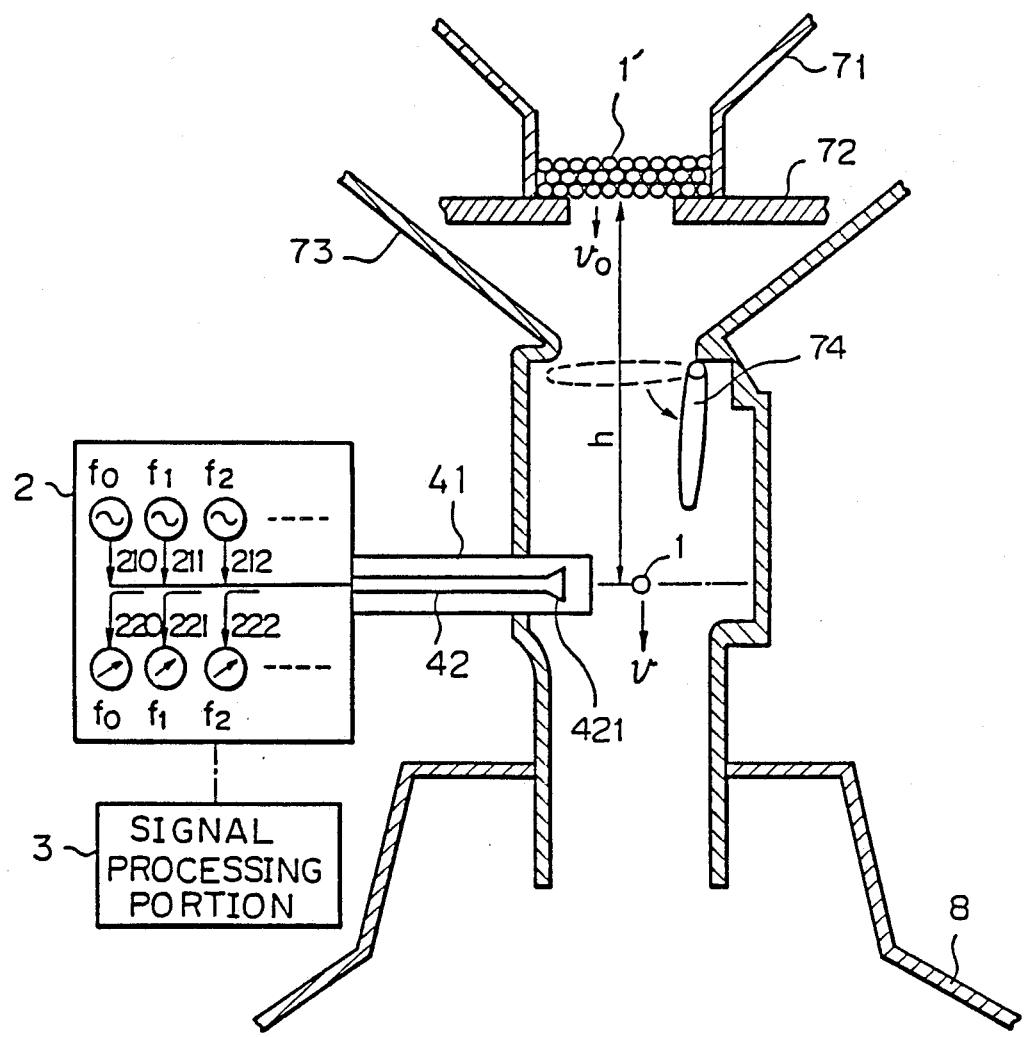
FIG. 1 shows an arrangement for transmitting electromagnetic waves onto particles in the falling state and the reflected electromagnetic waves at the top of a blast furnace according to an embodiment of the present invention.

Before describing in detail the embodiments of the present invention, the principle of the measurement of the sizes of particles in a falling state according to the present invention will be described with reference to FIGS. 1, 2, and 3. In FIG. 1, the arrangement for transmitting an electromagnetic wave in, for example, the microwave wavelength range, onto the particles in the falling state and receiving the reflected electromagnetic wave located at the top of a PW type blast furnace is shown.

Figure 2:
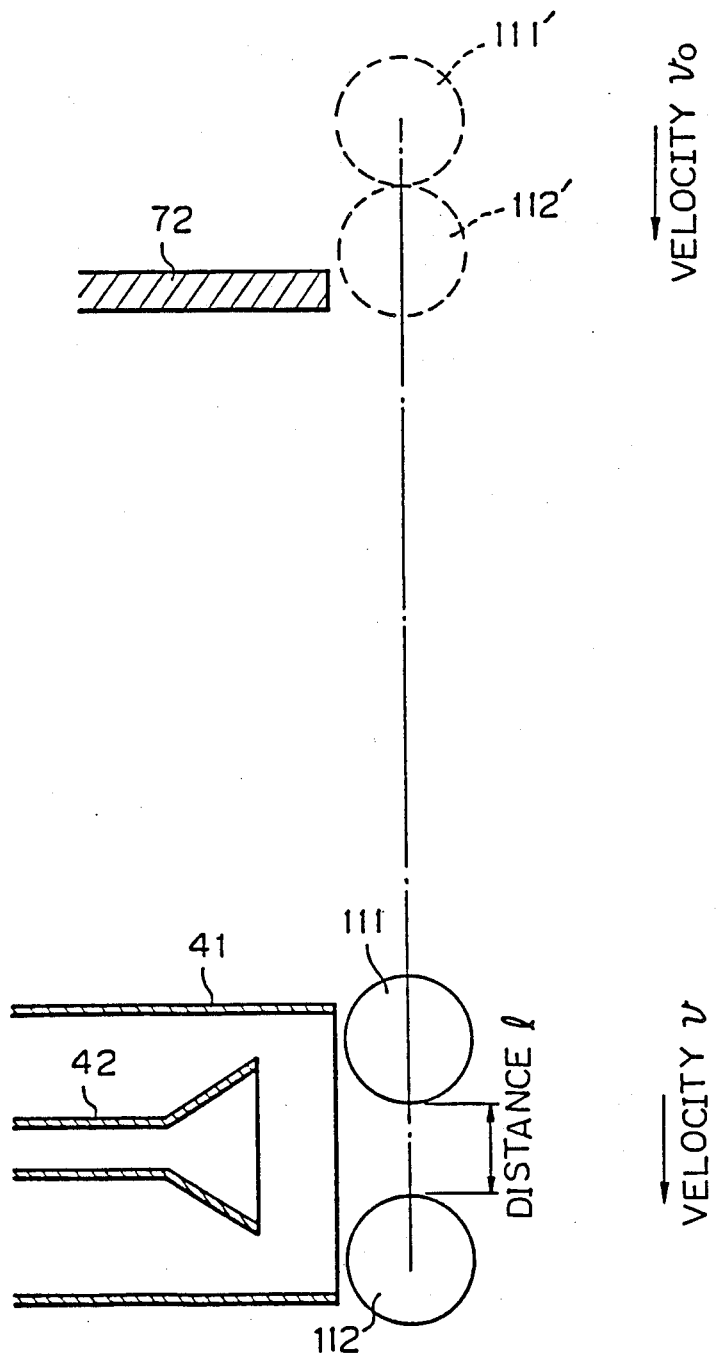
FIG. 2 shows a state of adjacent particles when falling from the outlet of the charging hopper to the level of the probe.

In FIG. 2, a state of the adjacent particles 111 and 112 when falling from the outlet of the charging hopper 71 to the level of the probe 41 is illustrated. The particles 111' and 112' are in contact with each other at the outlet of the charging hopper 71, the particles being shown in broken lines, and are separated by a distance "l" at the level of the probe 41, the separated particles 111 and 112 being shown by solid lines.

Figure 3:
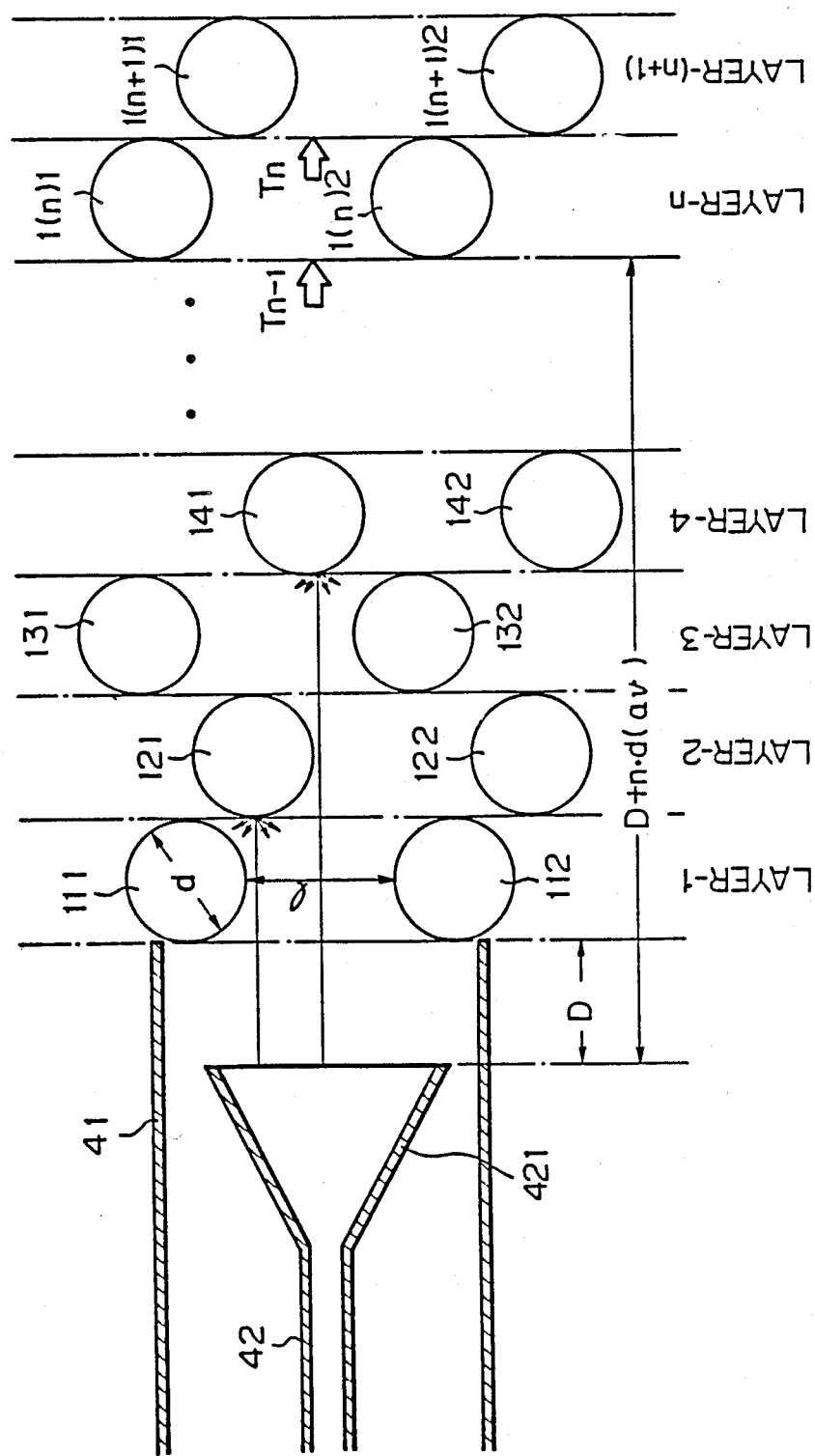
FIG. 3 shows the irradiation of the electromagnetic waves from an antenna in a waveguide and the reflection of the electromagnetic waves from the particles in the falling state.

In FIG. 3, the transmission of the electromagnetic wave from an antenna in a waveguide and the reflection of the electromagnetic wave from the particles in the falling state are illustrated.

FIG. 1 shows particles 1' in the stored state, particles 1 in the falling state, a transmitter/receiver 2, a signal processing portion 3, a probe 41, a waveguide 42, an antenna 421, a charging hopper 71, a dumper 72, a vertical chute 73, a gate 74, and a blast furnace 8. The transmitter/receiver 2 includes oscillators 210, 211, 212 . . . for frequencies $f_0$, $f_1$, $f_2$ . . . and detectors 220, 221, 222 . . . for frequencies $f_0$, $f_1$, $f_2$ . . . in the form of, for example, a square-law detector using diodes. The oscillators and the detectors are connected with the waveguide 42 via directional coupling devices.

FIG. 3 shows particles 111, 112 in layer-1; 121, 122 in layer-2; 131, 132 in layer-3; 141, 142 in layer-4; . . . 1(n)1, 1(n)2 in layer-n; and 1(n+1)1, 1(n+1)2 in layer-(n+1) in the falling state.

It is assumed that the level difference between the outlet of the charging hopper 71 and the probe 41, is h, and the initial velocity of a granule 1 when the granule 1 falls from the charging hopper 71 is $v_0$. As the result of free falling, the velocity v of the particle at the level of the probe 41 is expressed by the following equation, where g is the gravitational constant.

$$v = \sqrt{v_0^2 + 2gh} \quad (1)$$

As illustrated in FIG. 2, the distance between the adjacent particles 111 and 112 is increased from 0 at the outlet of the charging hopper 71 to "l" at the level of the probe 41. The distance "l" is expressed by the following equation, where "d" is the diameter of a particle.

$$l = d \cdot \frac{v - v_0}{v_0} \quad (2)$$

Thus, the distribution of the particles in front of the probe 41 can be expressed as shown in FIG. 3. The pairs of particles 111, 112; 121, 122; 131, 132; 141, 142; . . . 1n1, 1n2; and 1(n+1)1, 1(n+1)2 exist at random in front of the probe 41; the particles of each pair being spaced from each other by a vertical gap of length l.

It can be considered that the layers 1, 2, 3, . . . n, and (n+1), each including particles, are stacked from left to right, and the electromagnetic wave is irradiated from the antenna 421 onto this stack of layers.

It is assumed that the transmission rate of the electromagnetic wave which is transmitted through the layers from layer (1) to layer (n−1), is $T_{n-1}$, and the transmission rate of the electromagnetic wave which is transmitted through the layers from layer (1) to layer (n), is $T_n$. In the arrangement shown in FIG. 3, the following equations are obtained.

$$T_n = k \cdot T_{n-1} \quad (3)$$

That is, each time an electromagnetic wave passes through one layer of the particle layers, a portion of the electromagnetic wave is blocked by that layer, and accordingly, the electromagnetic wave is attenuated. In this equation (3), k is defined by equation (4) below, that is, k is the rate of the portion of the electromagnetic wave which has not been blocked when the electromagnetic wave passes through the one layer.

According to the first order approximation, k is expressed by the following equation.

$$k = \frac{l}{l + d} = \frac{v - v_0}{v} \quad (4)$$

According to equation (3), $T_1 = kT_0$, $T_2 = kT_1$, and so on. Since nothing exists in number-zero layer, the electromagnetic wave passes through the number-zero layer without any loss, and thus it is obvious that the transmission rate of the number-zero layer is "one". Accordingly, the value of $T_0$ is "1".

As a result, the following equation is derived.

$$T_n k^n \quad (5)$$

Hence, the reflection $R_n$ of the electromagnetic wave reflected from the surface of layer (n+1) is expressed as the following equation.

$$R_n = (k^n - k^{n+1}) \cdot \sigma_n \quad (6)$$

In this equation, $\sigma_n$ represents a scattering cross-section normalized by $$\frac{\pi}{4} d^2.$$

The $\sigma_n$ is determined by the size of the granule, the wavelength λ of the electromagnetic wave, the shape of the granule, and the like.

The electromagnetic wave is scattered radially (spherically) in all directions from the surface of the particles. The antenna 421 receives the electromagnetic wave reflected from the surface of layer (n+1) at the receiving rate $P_n$ expressed in equation (7) below. In equation (7), $d_a$ is the average size of particles.

$$P_n = \frac{A \cdot k^n \cdot R_n}{4\pi (D + n \cdot d_a)^2} = \frac{A \cdot k^n (k^n - k^{n+1})\sigma_n}{4\pi (D + n \cdot d_a)^2} \quad (7)$$

In this equation A is the area of the antenna 421. This equation means that the electromagnetic wave reflected from the surface of layer (n+1) propagates again through n layers and returns to the antenna 421, so that the electromagnetic wave is attenuated by factor $k^n$ derived from equations (3), (4) and (5), and that the electromagnetic wave reflected from the surface of layer (n+1) scatters spherically in all directions and returns to the antenna 421 so that the electromagnetic wave is also attenuated by factor $A/4\pi(D+n\cdot d_a)^2$, which is the ratio between the area A of the antenna 421 and the surface area $4\pi(D+n\cdot d_a)^2$.

In this equation, $d_a$ is the average size of the particles, which is expressed aes $d_a=\Sigma d_i/n$, and D is the distance between the end of the antenna 421 and the end of the probe 41.

The amount of all electromagnetic waves reflected and returned to the antenna is the sum of the amounts of electromagnetic waves reflected from all layers. Hence, the reflectance $R_{ant}$ of the electromagnetic wave at the antenna 421, and the related amounts, are expressed by the following equations, provided that the change of the scattering cross-section $\sigma_n$ is small and the scattering cross-section is approximately equal to a constant value $\sigma_{const}$.

$$R_{ant} = \sum_{1}^{\infty} \frac{Ak^n(k^n - k^{n+1})\sigma_n}{4\pi(D + n \cdot d_a)^2} = \frac{\sigma_{const}}{d_a^2} \cdot K \tag{8}$$

$$D = \theta \cdot d_a \tag{9}$$

$$K = \sum_{1}^{\infty} \frac{AK^n(k^n - k^{n+1})}{(\theta + n)^2} \tag{10}$$

In general, the spherical reflection of the electromagnetic wave is not carried out isotropically. Hence, in practice, the following equation (11) presents the actual condition.

$$R_{ant} = \frac{\sigma_{const}}{d_a^{2+\alpha}} \cdot K \tag{11}$$

In this equation, $\alpha$ is a parameter satisfying the inequality $0<\alpha<2$ and is determined generally from the result of experiments.

The scattering cross-section $\sigma$ increases quickly and monotonously with a power in the range spanning more than the second power and less than the fourth power of $d_a$ according to the increase of $d_a$ when $d_a$ is smaller than 0.4 λ, and converges, through an oscillation of the value around 1, to "1", when $d_a$ exceeds 0.4 λ.

The reason is that, since $\alpha$ is given as $0<\alpha<2$, the $d_a^{2+\alpha}$ in equation (11) is between the second power $d_a^2$ and the fourth power $d_a^4$.

Figure 4:
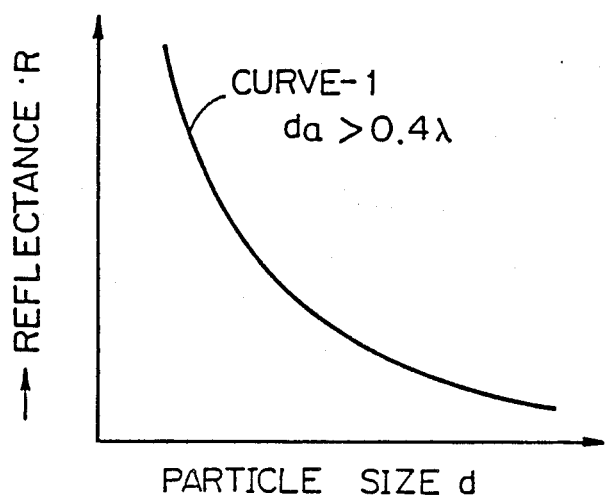
FIG. 4 shows the relationship between the size of the particles and the reflectance of the electromagnetic waves.
Figure 4:
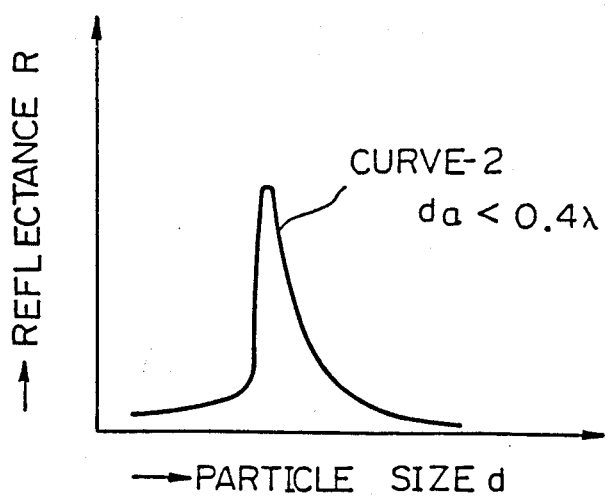

The relationship between the size of the granule and the reflectance of the electromagnetic wave R is shown in FIG. 4. The monotonous decreasing of the reflectance for $d_a>0.4$ λ is represented by curve-1, and the reflectance having a peak value in the middle for $d_a<0.4$ λ is represented by curve-2.

By measuring the reflectance by using a first electromagnetic wave having a frequency $f_0$ satisfying the inequality $d_a \geq 0.4$ λ and a second electromagnetic wave having the frequencies $f_1, f_2, \ldots f_n$ satisfying the inequality $d_a<0.4$ λ, it is possible to measure the distribution of the sizes of the particles.

The definition of the reflectance R of the electromagnetic wave by the particles will now be described. Since the propagation mode of the electromagnetic wave might be changed at an antenna portion of a waveguide, at bent portions of a waveguide, or at like portions, the electromagnetic wave will be necessarily reflected at these portions. Hence, even if there are no articles which reflect the electromagnetic wave existing in front of the antenna, a value of the reflection power will be detected. It is possible to make the detected reflection power to be zero when no granule exists in front of the antenna by providing a compensation means such as a stub tuner in the waveguide. In this case, the average value over a predetermined time period of the detected reflectance when particles exist in fron of the antenna is adopted as the reflectance regarding the particles.

In practice, however, it is difficult to maintain the detected reflection power as strictly zero when no granule exists in front of the antenna. Hence, some consideration is required for the case of other than zero. In this case, an effective reflectance obtained by the following equation is adopted as the reflectance regarding the particles.

$$R_{eff} = FUNC(R) \tag{12}$$

In this equation, $R_{eff}$ is an effective reflectance, R is a detected reflectance, and FUNC(R) is a function operating the degree of change of R with time. The definition of the function FUNC is related, for example, to time deivation expressed by the following equation, where X(t) is the instantaneous value and $x_a$ is the average value of the reflectance.

$$FUNC(x) = \sqrt{\frac{\int_{t1}^{t2}(x(t) - x_z^2)dt}{(t2 - t1)}} \tag{13}$$

In consequence, the method and apparatus according to the present invention are based on the above-described principle of the measurement of the sizes of the particles in the falling state.

An apparatus for measuring the sizes of the particles in the falling state according to a preferred embodiment of the present invention is illustrated in FIGS. 1, 2, and 3. In the apparatus shown in FIG. 1, an electromagnetic wave of multiple frequencies generated in the transmitter/receiver 2 is applied to the particles 1 in the falling state.

It is assumed that the falling particles consist of a volumetric fraction x of particles having a size $d_0$, a volumetric fraction y of particles having a size $d_1$, and a volumetric fraction z of particles having a size $d_2$. The sum of x, y, and z is equal to 1 (x+y+z=1). The measurement of the distribution of the sizes of particles is obtained by using three frequencies, $f_0$, $f_1$, and $f_2$. Frequency $f_0$ is selected to satisfy the condition $d_a>0.4$ λ for CURVE-1, and frequencies $f_1$ and $f_2$ are selected to satisfy the condition $d_a<0.4$ λ for CURVE-2 (FIG. 4).

Figure 5:
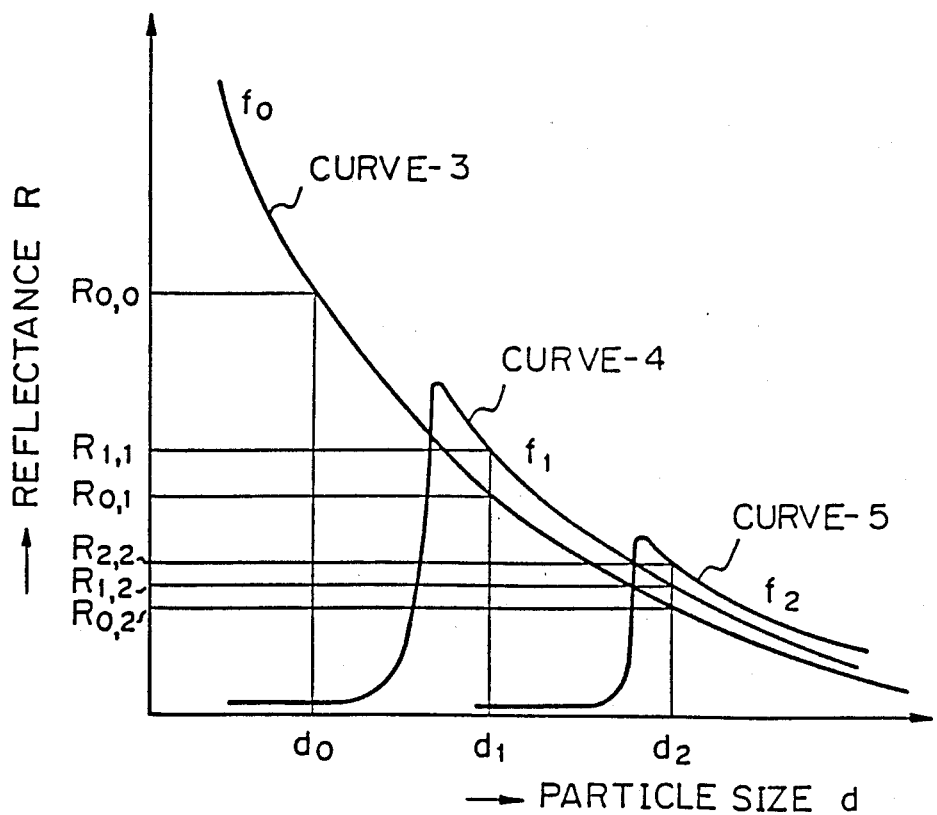
FIG. 5 shows the relationship between the size of the particles and the reflectance of the electromagnetic waves where particles of different sizes are mixed.

The relationship between the granule size d and the reflectance rate R is shown in FIG. 5. With regard to the reflectance for frequency $f_2$, there is no reflecting power from particles having a size $d_0$, or $d_1$, but only from particles having a size $d_2$. With regard to the reflectance for frequency $f_1$ no reflecting power is obtained from particles having a size $d_0$, but is gained from particles having a size $d_1$ or $d_2$. With regard to the reflectance for frequency $f_0$, a reflecting power is obtained from particles having a size $d_0$, $d_1$, or $d_2$.

In the apparatus shown in FIG. 1, electromagnetic waves having the frequencies $f_0$, $f_1$, and $f_2$ are transmitted from the transmitter/receiver 2 through the waveguide 2 with the horn antenna 421 into the mixture of particles 1 having the sizes $d_0$, $d_1$, and $d_2$ in the falling state.

The reflectance $R_0$ represents the rate of reflection of the electromagnetic wave having the frequency $f_0$ from the mixture of particles. The reflectance $R_1$ represents the rate of reflection of the electromagnetic wave having the frequency $f_1$ from the particles having sizes $d_1$ and $d_2$ in the mixture of particles. The reflectance $R_2$ represents the rate of reflection of the electromagnetic wave having the frequency $f_2$ from the particles having size $d_2$ in the mixture of particles.

The reflectance $R_{i,j}$ represents the rate of reflection of the electromagnetic wave having the frequency $f_i$ from particles having a uniform size $d_j$.

When the electromagnetic waves having the frequencies $f_0$, $f_1$, and $f_2$ are transmitted onto the particles having the sizes $d_0$, $d_1$, and $d_2$, the volumetric fraction Z of the particles having the size $d_2$ is given by the following equation.

$$Z = \frac{R_2}{R_{2,2}} \quad (14)$$

The particles having the size $d_1$ and the particles having the size $d_2$ contribute to the reflectance $R_1$.

The contribution of the particles having the size $d_2$ should be subtracted by using the calculated Z to obtain the volumetric fraction y, as expressed in the following equation.

$$y = \frac{R_1 - R_{1,2} \cdot z}{R_{1,1}} \quad (15)$$

The contribution of the particles having the size $d_1$ and the particles having the size $d_2$ should be subtracted by using the calculated y and z to obtain the volumetric fraction x, as expressed in the following equation.

$$z = \frac{R_0 - R_{0,1} \cdot y - R_{0,2} \cdot z}{R_{0,0}} \quad (16)$$

A process of calculation of the average size d(av) of the particles, using the single frequency $f_0$, will be described below. Assuming that the total volume of the particles is V, and the number of particles having size $d_j$ is $N_j$, the number $N_j$ is given by the following equation.

$$N_j = \frac{6V}{\pi d_j^3} \quad (17)$$

The reflectance $R_{0,j}$ is expressed approximately by the following linear equation, if the range of granule sizes to be measured is limited to some extent.

$$R_{0,j} = \xi \cdot d_j + \eta \quad (18)$$

By using particles having a uniform size, the values $\xi$ and $\eta$ can be preliminary determined.

It is assumed that $n_j$ particles exist having the size $d_j$, in a mixture of the particles. The total volume V of the particles is given by the following equation.

$$V = \sum_j n_j \left( \frac{\pi}{6} d_j^3 \right) \quad (19)$$

The reflectance $R_0$ is given by the following equation.

$$R_0 = \sum_j \frac{n_j}{N_j} \cdot R_{0,j} \quad (20)$$

By applying the equations (17), (18), and (19) to the equation (20), the following equations are derived.

$$\begin{aligned} R_0 &= \sum_j \frac{n_j}{N_j} \xi d_j + \eta \\ &= \xi \cdot \frac{\sum_j n_j \frac{\pi}{6} \cdot d_j^3 \cdot d_j}{\sum_j n_j \frac{\pi}{6} \cdot d_j^3} + \eta \\ &= \xi \cdot d_a + \eta \end{aligned} \quad (21)$$

$$d(av) = \frac{\sum_j n_j \frac{\pi}{6} \cdot d_j^3 \cdot d_j}{\sum_j n_j \frac{\pi}{6} \cdot d_j^3} \quad (22)$$

The value d(av) can be expressed as the volumetric average value of the size of the particles. Thus, the volumetric average size $d_a$ can be calculated by measuring $R_0$ and using the preliminary obtained $\xi$ and $\eta$ according to the following equation.

$$d_a = \frac{R_0 - n}{\xi} \quad (23)$$

The electromagnetic wave in the microwave wavelength range having the frequencies $f_0$, $f_1$, $f_2$ is transmitted from the antenna 421 onto the particles 1 in the falling state when delivered from the charging hopper 71. The electromagnetic wave reflected from the particles in the falling state is received by the transmitter/receiver 2 through the waveguide 42 with the antenna 421, and the received signal is supplied to the signal processing portion 3. In the signal processing portion 3, the reflectance of the electromagnetic wave reflected from the particles is calculated, and the distribution of the sizes of the particles and the average size of the particles are calculated according to the above-described equations.

An example of the sequence of processes for determining the distribution of sizes of the particles using three frequencies in the signal processing portion 3 is described below.

(i) Supposing an example of the mixture of the particles to be measured, select representative particle sizes $d_0$, $d_1$, and $d_2$.

(ii) Select $f_0$ so as to satisfy the condition $d_a > 0.4\lambda$ (FIG. 4, CURVE-1). Select $f_1$ and $f_2$ so as to satisfy the condition $d_a < 0.4\lambda$ (FIG. 4, CURVE-2).

(iii) By using electromagnetic waves having the frequencies $f_0$, $f_1$, and $f_2$, and particles having a uniform particle size, obtain CURVES-3, 4, and 5 (FIG. 5) in accordance with the change of particle size.

(iv) Obtain $R_{0,0}$, $R_{0,1}$, $R_{0,2}$, $R_{1,1}$, $R_{1,2}$, and $R_{2,2}$ from CURVES-1, and 2 (FIG. 4) in correspondence with the selected representative particle sizes $d_0$, $d_1$, and $d_2$.

(v) Measure the reflectances $R_0$, $R_1$, and $R_2$ corresponding to the frequencies $f_0$, $f_1$, and $f_2$ by the apparatus of FIG. 1.

(vi) Obtain the proportions x, y, and z in the mixture of particles from the obtained $R_{0,0}$, $R_{0,1}$, $R_{0,2}$, $R_{1,1}$, $R_{1,2}$, and $R_{2,2}$ and the measured $R_0$, $R_1$, and $R_2$.

It is possible to modify the apparatus of FIG. 1 in the manner shown in FIGS. 6, 7, 8, and 9.

Figure 6:
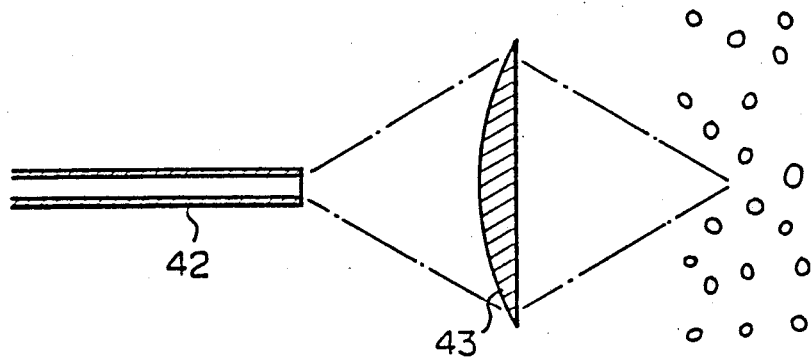
FIG. 6 shows a modified apparatus in which a dielectric lens is used.

In FIG. 6, a dielectric lens 43 is arranged in front of the waveguide 42. It is also possible to omit the dielectric lens from the arrangement shown in FIG. 6.

Figure 7:
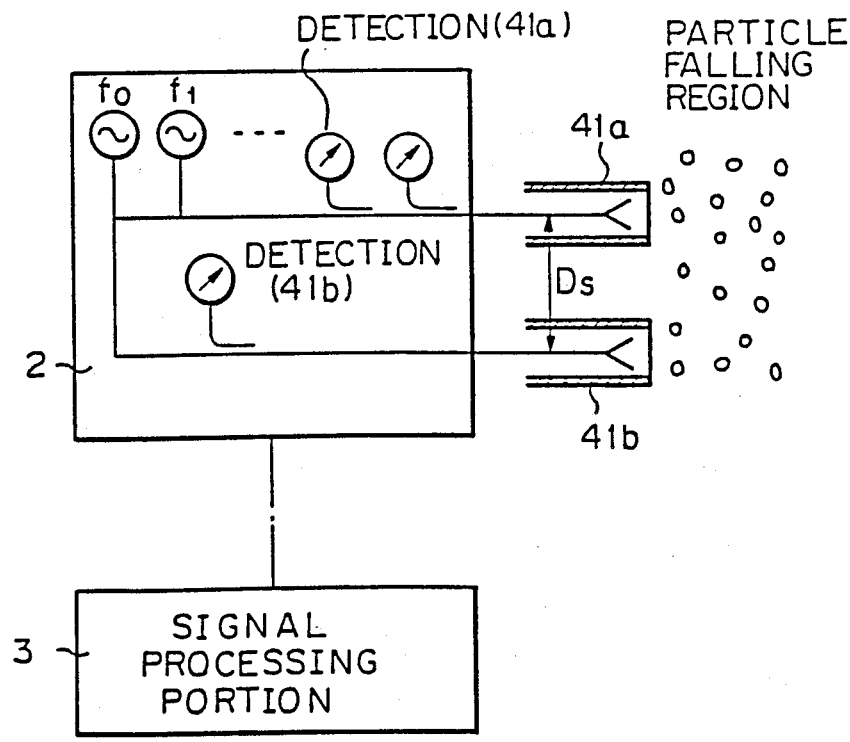
FIG. 7 shows a modified apparatus in which two probes are used.
Figure 8:
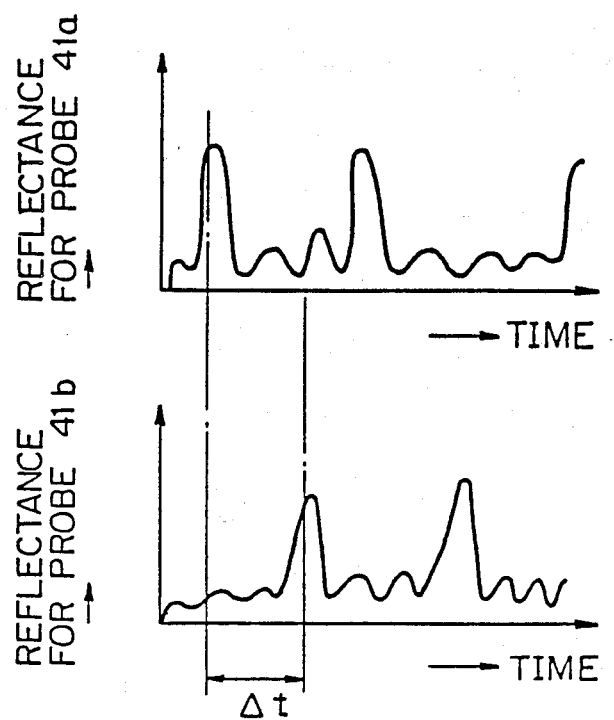
FIG. 8 shows the reflectances (reflectance) with regard to time for the two probes.

In FIG. 7, a lower additional probe 41b is arranged at a distance $D_s$ below the probe 41a. The correlation treatment is carried out for treating the result of the measurement by the arrangement of FIG. 7.

The cross correlation $C(\tau)$ is expressed by the following convolution equation.

$$C(\tau) = R(t) \cdot R(t-\tau) \cdot dt \tag{24}$$

Assuming R(t) is the signal from the probe 41a, and $R(t-\tau)$ is the signal from the probe 41b, the correction time $\tau$, which makes $C(\tau)$ maximum, corresponds to the time-delay $\Delta t$ between the probes 41a and 41b. The average velocity $v_a$ is expressed by the following equation.

$$v_a = \frac{D_s}{\Delta t} \tag{25}$$

Hence, the average velocity $v_a$ between the probes 41a and 41b can be calculated according to this equation.

The velocity v of the particle in front of the probe 41a is expressed as follows.

$$v = v_a - \frac{g \cdot D_s}{2 V_a} \tag{26}$$

By applying equation (26) to equation (1), the initial velocity $v_0$ is calculated by the following equation.

$$v_0 = \sqrt{\overline{v_a - \frac{g \cdot D_s}{2 V_a}}^2 - 2gh} \tag{27}$$

Figure 9:
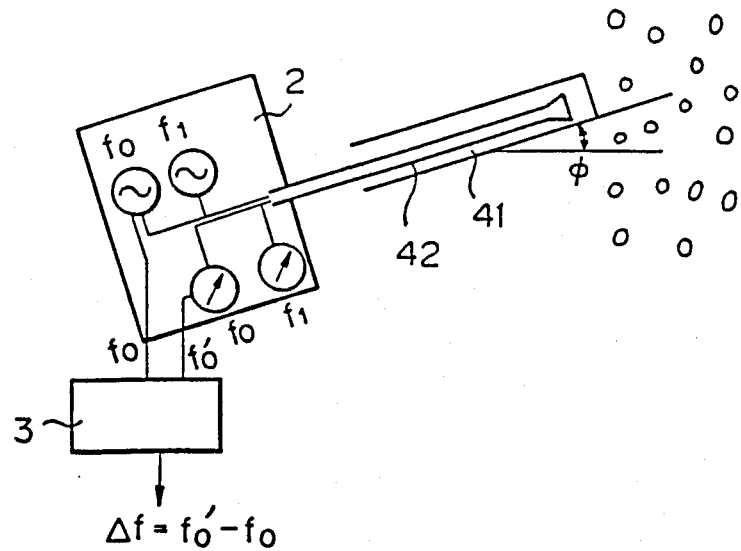
FIG. 9 shows a modified apparatus in which the Doppler effect is used.

In FIG. 9, the probe 41 is arranged at an angle $\phi$ with respect to the horizontal line. The electromagnetic wave having the frequency $f_0$ is transmitted onto the particles in the falling state. The frequency of the reflected electromagnetic wave reflected from the particles in the falling state is detected as $f_0'$, as the result of the Doppler effect. The frequency difference $\Delta f$ between $f_0$ and $f_0'$ is expressed by the following equation, where C is the velocity of light:

$$\Delta f = f_0' - f_0 \tag{28}$$
$$= \frac{v \cdot \sin\phi}{C}$$

(since $\Delta f = \Delta v/C$ and $\Delta v$ is the component of falling velocity in the direction of the electromagnetic wave transmission which is equal to $v\sin\phi$ where v is the falling velocity in the vertical direction.)

Hence, the following equation is derived.

$$v = \frac{\Delta f \cdot C}{\sin\phi} \tag{29}$$

By applying equation (29) to equation (1), the following equation is derived.

$$v_0 = \sqrt{\overline{\frac{\Delta f \cdot C}{\sin\phi}}^2 - 2gh} \tag{30}$$

Hence, where the initial velocity $v_0$ changes, it is possible to calculate the initial velocity $v_0$ by measuring the falling velocity v. Therefore, it is possible to calculate $$\frac{v - v_0}{v}$$

from the calculated initial velocity $v_0$, and accordingly, to calculate the value of K defined by equation (10).

Figure 10:
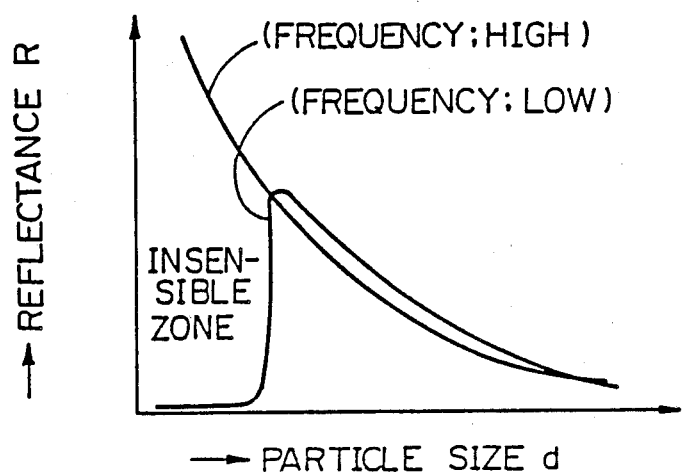
FIG. 10 shows the relationship between the size of the particle and the reflectances (reflectance) where a frequency sweep using a single oscillator is carried out.
Figure 11:
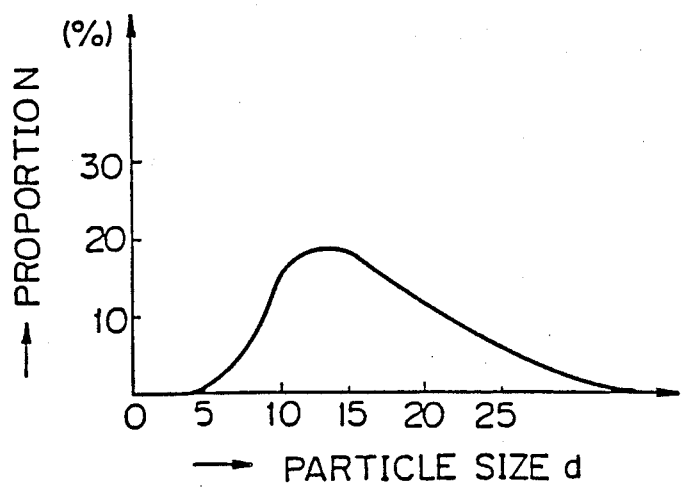
FIG. 11 shows the distribution of the sizes of the particles.

Alternatively, it is possible to measure the distribution of the sizes of the particles by a frequency sweep process using a single oscillator, where the distribution of sizes of the particles does not change during the measurement period of, for example, several seconds. In this case, the relationship between the particle size d and the reflectance R changes continuously, as shown in FIG. 10. The insensible zone where the reflecting power is very small will be expanded continuously as the frequency is changed from high to low. Consequently, the distribution of the sizes of the particles can be continuously measured as shown in FIG. 11.

Examples of the structure of the probe will be described with reference to FIGS. 12, 13, and 14. An example of the combination of a probe and a protector will be described with reference to FIG. 15.

In the structures shown in FIGS. 12 to 15, the probe 41, which is located in the region where the particles are falling, is made of an impact-resistant metal cylinder. A waveguide 42 with the antenna 421 supported by support plates 451 and 452 is accommodated in the probe 41. One end of the waveguide 42 is connected with the transmitter/receiver 2 (FIG. 1). The antenna 421 may be horn-shaped or cylindrical.

Figure 12:
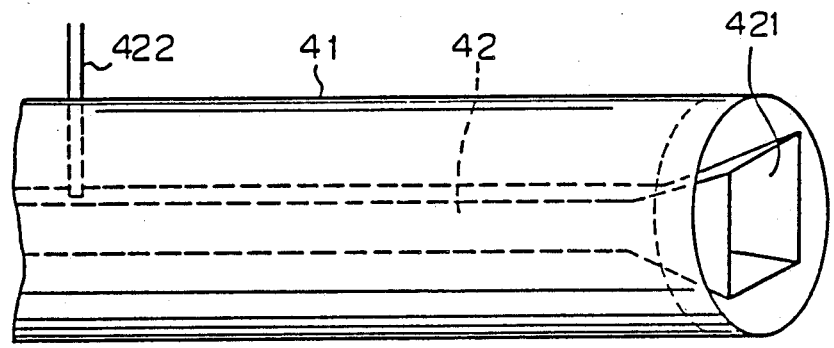
FIGS. 12, 13, and 14 show modified probes used for the apparatus according to the present invention.
Figure 13:
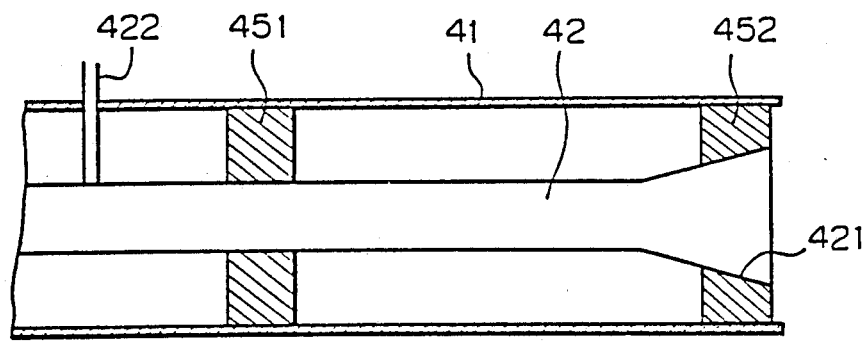

It is possible to introduce a gas for purging, such as air, inert gas, or the like, into the waveguide 42 through a supply pipe 422 and purge the introduced gas from the waveguide 42 through the end of the antenna 421 as shown in FIGS. 12 and 13. This introduction and purging of the gas for purging prevents the particles, the dust, and the like from invading the waveguide 42.

Figure 14:
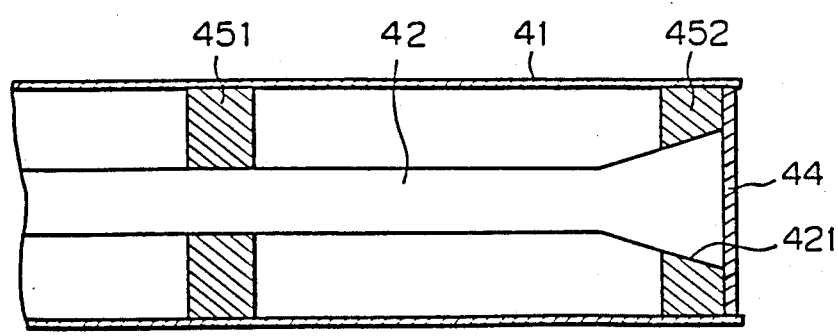

It is possible to provide a lid 44 made of an electromagnetic wave transmitting material, such as quartz glass or the like, at the end of the antenna 421 as shown in FIG. 14. The lid 44 prevents the particles or dust from invading the waveguide 42.

The external surface of the lid 44 is likely to be contaminated by the particles, the dust, and the like while the apparatus is operated. Accordingly, it may be necessary to clean the external surface of the lid at predetermined intervals.

Figure 15:
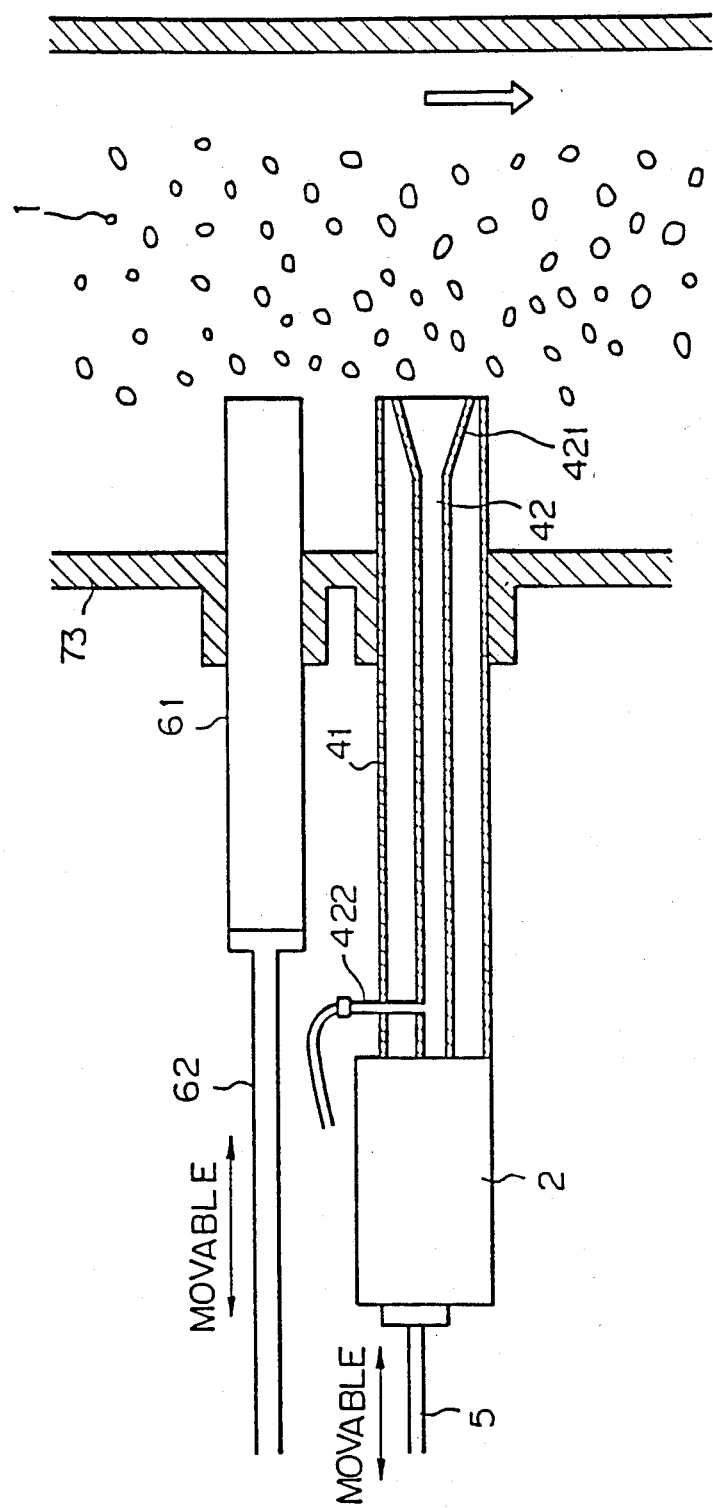
FIG. 15 shows a modified probe having a protector used for the apparatus according to the present invention.

In FIG. 15, the combination of the probe 41 and a protector 61 is shown. The protector 61 is located over the probe 41 to prevent the falling particles from colliding with the probe 41 and exerting a resulting strong impact shock on the probe 41.

The ends of the protector 61 and the probe 41 are projected through the wall of the vertical chute 73 into the particle falling region. In order to facilitate the measurement of the size of th particles at desired positions, there are provided a piston 62 for moving the protector 61 and a piston 5 for moving the transmitter/receiver 2 and the probe 41. Each of the pistons 62 and 5 is driven by a driving mechanism such as an electric motor, a hydraulic cylinder, or the like.

It is possible to modify the apparatus of FIG. 1 to include a calibration arrangement in the apparatus, to ensure that the transmitter/receiver has a constant gain. The factors causing changes in the gain are the electromagnetic wave transmission output, the receiver diode sensitivity, the waveguide attenuation, the reflection at the end of the antenna, and the like.

Figure 16:
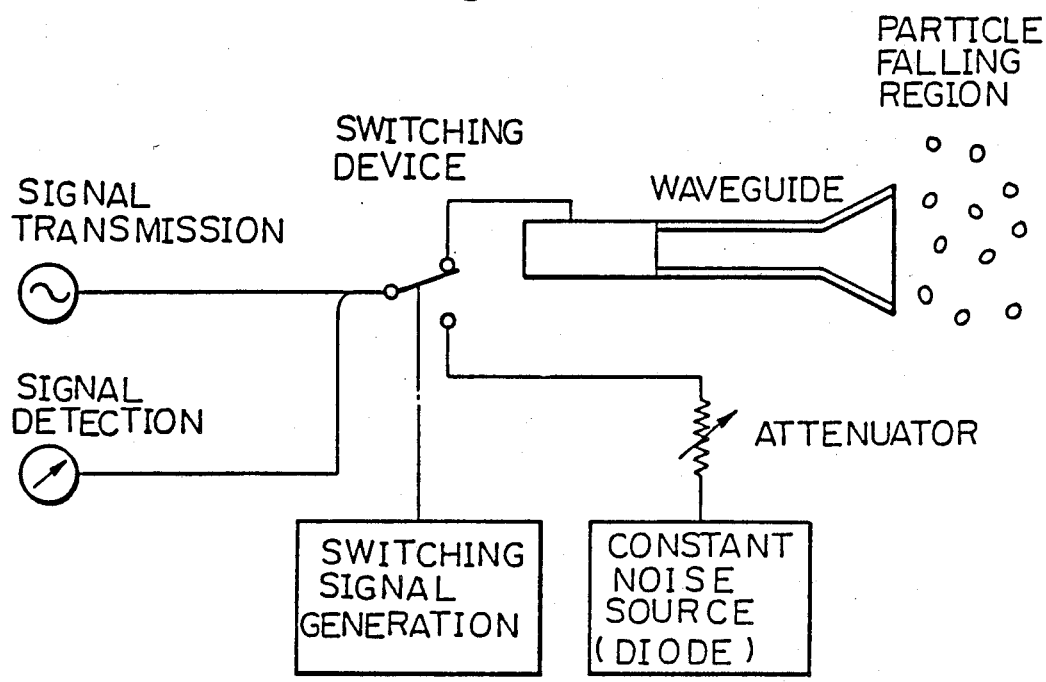
FIG. 16 shows an inner calibration device used in a modified apparatus according to the present invention.
Figure 17:
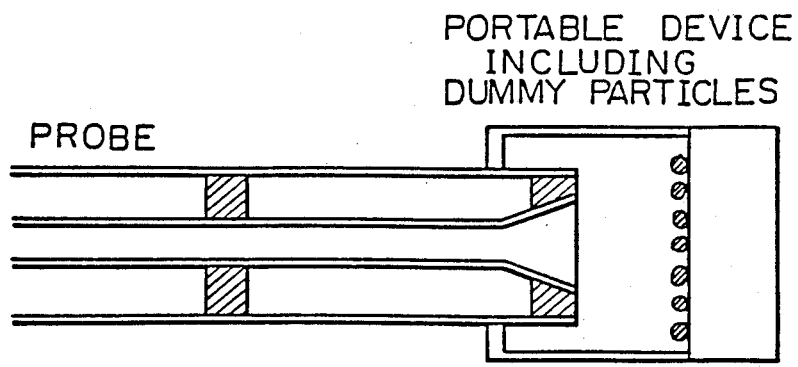
FIG. 17 shows an external calibration device use in a modified apparatus according to the present invention.

In order to eliminate these factors causing the changes in the gain, a calibration arrangement such as an internal calibration arrangement shown in FIG. 16 and an external calibration arrangement shown in FIG. 17 is used. The internal calibration arrangement shown in FIG. 16 includes a switching device actuated by a switching signal generation portion, an attenuator, and a constant noise source using, for example, a diode. The gain of signal detection in the signal detection portion is automatically regulated in such a manner that the reference reflection from the internal calibration device is always rendered as a constant output signal. Preferably, the internal calibration is carried out before each measurement with regard to one dump of the particles.

The external calibration arrangement shown in FIG. 17 is samples for which the reflectance of the electromagnetic wave is shown. By attaching the portable device at the end of the probe, the detection of whether or not the detection signal of the reflection electromagnetic wave is reflected from the dummy particle samples is maintained as constant. If a variation in the detection signal is detected, it is determined whether there exists abnormalities in the end portion of the probe, in the waveguide, or the like. The external calibration arrangement is disclosed to the checking of the external exposed portions, such as a coaxial cable, a waveguide, a probe, or the like. The calibration by the external calibration arrangement may be carried out by maintenance personnel while the blast furnace is inactive. It is possible to carry out the transmission and reception of electromagnetic waves having different frequencies by a frequency sweep process using a single oscillator, instead of the above-described use of a plurality of oscillators having different frequencies.

Figure 18:
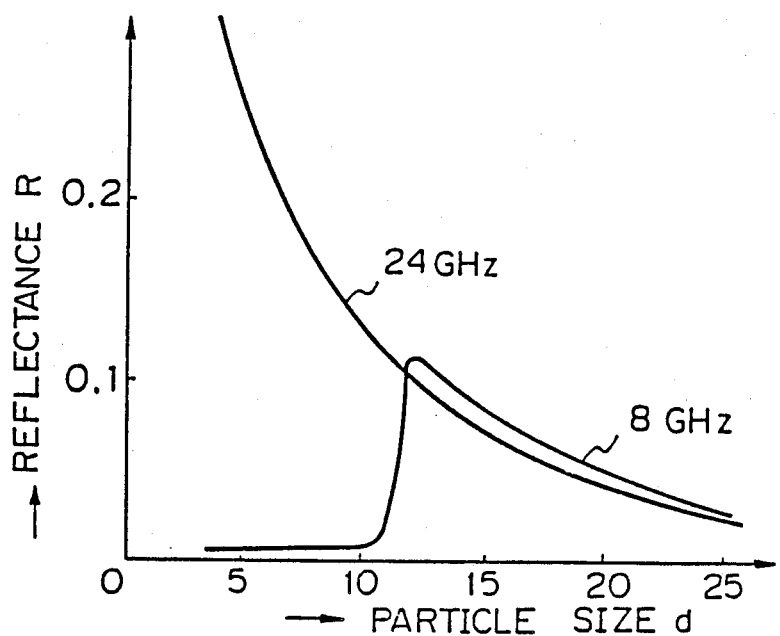
FIG. 18 shows the result of an experiment representing the relationship between particle size and the reflectance.
Figure 19:
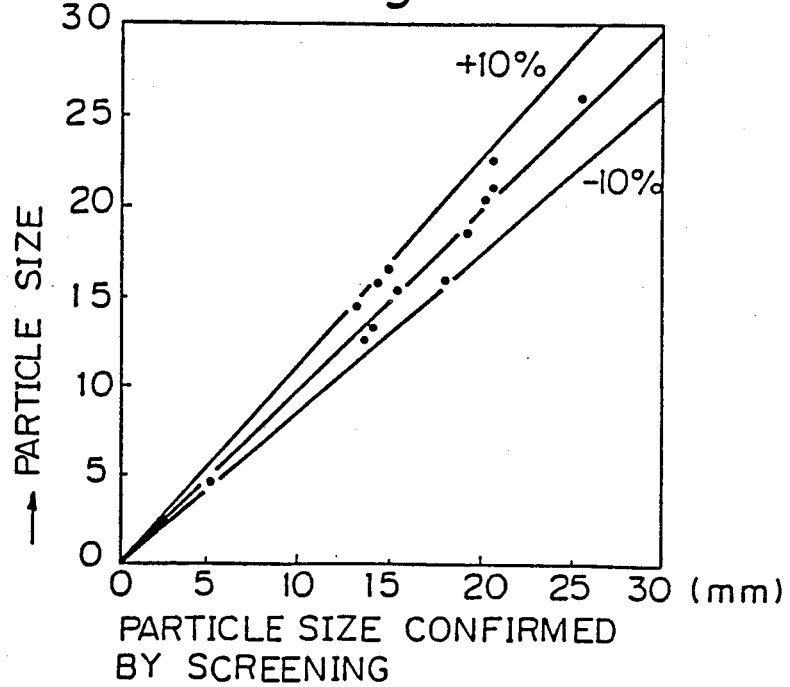
FIG. 19 shows the result of an experiment representing the relationship between the particle size confirmed by screening and the reflectance.

An example of the result of a test of the operation of an apparatus in the form of a model of the apparatus of FIG. 1 according to the present invention will be described below. In the test, microwave of 24 GHz and 8 GHz are transmitted from the antenna to the particles in the falling state. The distance h is 1660 mm, the initial velocity $v_0$ of the granule is 1.5 m/s, and the velocity v of the falling particles in front of the probe is 5.9 m/s. The result of the test is shown in FIG. 18 in the form of the relationship between the particle size d and the reflectance R. The curve for 24 GHz expresses that the reflectance R is decreased monotonously with the increase of the granule size for sizes greater than 4 mm. The curve for B 8 GHz expresses that the monotonous decrease of the reflectance begins only when the particle size becomes greater than 12 mm and the reflectance is very small when the particle size is less than 10 mm. The characteristic of the curves in FIG. 18 is not necessarily proportional to $1/d^2$, since the characteristic of the efficiency of the antenna and the like. However, the same characteristic is attained as long as the same antenna and the same probe are used. Therefore, the curves in FIG. 18 can be used for the calibration curves for determining the sizes of the particles.

The relationship between the result of the measurement of the sizes of the particles using the calibration curves as shown in FIG. 18 and the result of the confirmation of the sizes of the particles by screening after the sampling of the falling particles is shown in FIG. 18. It can be seen that the measurement of the sizes of the particles can be carried out with a precision of ±10%.

Figure 20:
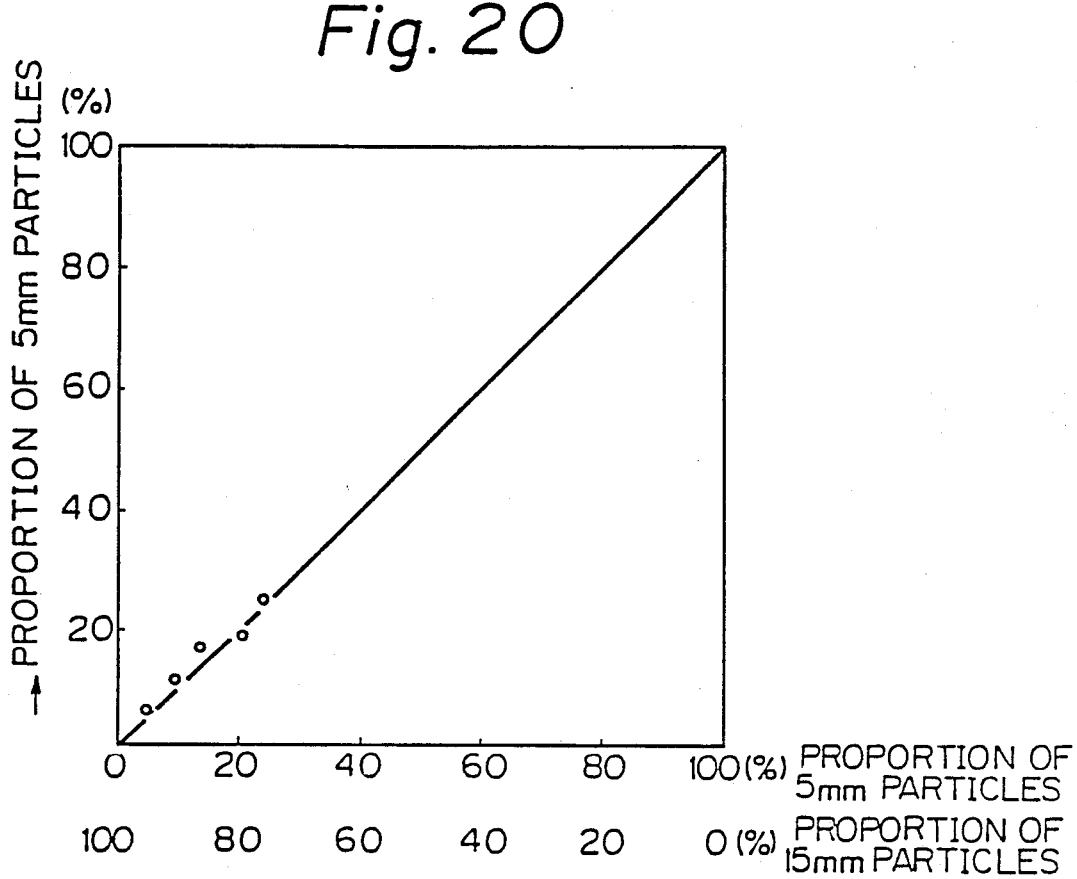
FIG. 20 shows the result of an experiment representing the relationship of various mixtures of different sizes of particles and the proportion of particles having a predetermined particle size.

An example of the result of the test of the operation of an apparatus in the form of a model of the apparatus of FIG. 1 according to the present invention, by changing the ratio between the particles having a size of 5 mm and the particles having a size of 15 mm, is shown in FIG. 20, and the result shown in FIG. 20 indicates that the method according to the present invention can be used practically to a great extent. If the number of frequencies of the electromagnetic wave is increased to three, four, and so on, the size of the particles can be measured even more precisely, and further, the distribution of the sizes of the particles can be obtained.

Figure 21:
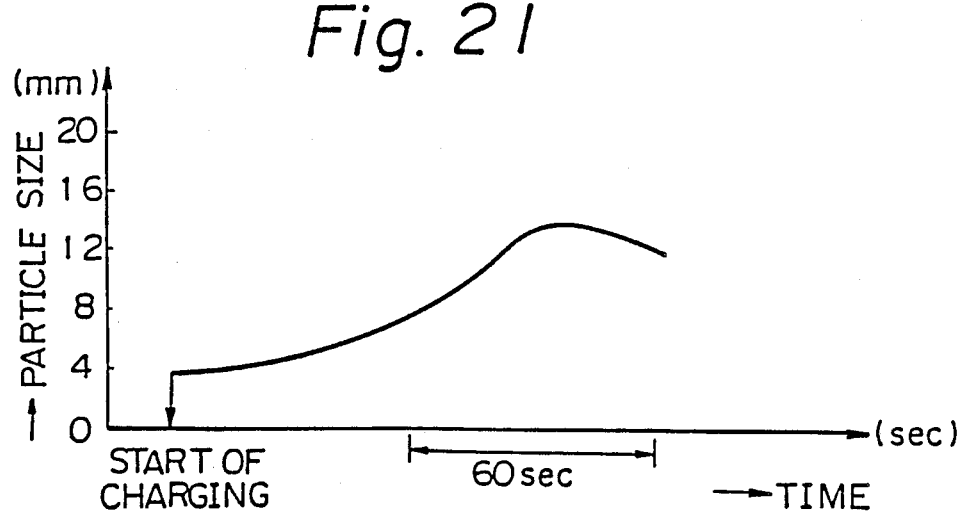
FIG. 21 shows the result of an experiment representing the change of particle size with regard to operation time of a blast furnace.

In general, in the prior art, the sintered ores having a size less than 5.5 mm are returned as return-fines to the original material storing vessel without being charged into the blast furnace, in order to ensure the transmission of air through the blast furnace and a stable running of the blast furnace. However, it is now possible to precisely detect variations of the sizes of the particles in one dump by using the method and apparatus according to the present invention. Consequently, it is possible to control the position where the fine ores are charged to achieve the stable running even if the criteria for the return-fines is selected as 4 mm. An example of the result of the measurement of the variation of the sizes of the particles in one dump is shown in FIG. 21.

Although certain preferred embodiments have been shown and described, it should be understood that many changes and modifications may be made therein without departing from the scope of the appended claims.

We claim:

1. An apparatus for measuring sizes of particles in the falling state comprising:

electromagnetic wave transmission and reception means for transmitting electromagnetic waves having different frequencies onto particles in the falling state at a predetermined angle with respect to the particle falling direction and receiving the electromagnetic waves having different frequencies reflected from said particles in the falling state;

detection means for detecting the intensities of said received electromagnetic waves having different frequencies and outputting signals; and signal processing means for processing said signals to derive data on the distribution of sizes of said particles and an average size of said particles, said signal processing means deriving the data based on the fact that said detected intensities are related to the sizes of said particles, the frequencies of said electromagnetic waves and the vertical gaps between said particles which are dependent on the particle sizes, an initial velocity of a respective one of the particles and a velocity of the respective particle in the falling state.

2. An apparatus according to claim 1, further comprising a drive mechanism for driving forward or rearward said electromagnetic wave transmission and reception means against the particles in the falling state.

3. An apparatus according to claim 1, wherein said electromagnetic wave transmission and reception means includes a probe and a protection member for covering said probe to prevent the falling particles from colliding with said probe.

4. An apparatus according to claim 1, wherein said electromagnetic wave transmission and reception means includes a calibration means for calibrating the gain of said electromagnetic wave transmission and reception means.

5. An apparatus according to claim 1, wherein said electromagnetic wave transmission and reception means consists of a first and second electromagnetic wave transmission and reception means, and said first and electromagnetic wave transmission and reception means includes an upper waveguide and said second electromagnetic wave transmission and reception means includes a lower waveguide.

6. An apparatus according to claim 1, wherein said signal processing means comprises means for deriving said data by calculating reflectances, each of the reflectances corresponding to a respective one of the frequencies of the transmitted electromagnetic waves, the reflectance at each of the frequencies corresponding to a particle size, and said signal processing means comprises means for deriving the distribution of the particles based on the reflectances.

7. An apparatus according to claim 1, wherein said electromagnetic wave transmission and reception means transmits electromagnetic waves having frequencies in the microwave wave length range, and the electromagnetic waves are transmitted by means of at least one antenna.

8. An apparatus according to claim 1, wherein said electromagnetic wave transmission and reception means transmits at least one electromagnetic wave having a frequency smaller than $d_a/4.0$, where the $d_a$ is the average size of the particles.

* * * * *